(12) United States Patent
Camacho et al.

(10) Patent No.: US 11,279,908 B2
(45) Date of Patent: Mar. 22, 2022

(54) APPARATUS AND METHOD FOR REFRACTORY ORGANICS CONVERSION INTO BIOGAS

(71) Applicant: SUEZ GROUPE, Paris la Défense (FR)

(72) Inventors: Patricia Camacho, Croissy sur Seine (FR); Mathieu Haddad, Rueil Malmaison (FR)

(73) Assignee: SUEZ GROUPE, Paris la Défense (FR)

( * ) Notice: Subject to any disclaimer, the term of this patent is extended or adjusted under 35 U.S.C. 154(b) by 196 days.

(21) Appl. No.: 16/630,808

(22) PCT Filed: Jul. 30, 2018

(86) PCT No.: PCT/EP2018/070639
§ 371 (c)(1),
(2) Date: Jan. 13, 2020

(87) PCT Pub. No.: WO2019/025390
PCT Pub. Date: Feb. 7, 2019

(65) Prior Publication Data
US 2020/0165553 A1    May 28, 2020

Related U.S. Application Data

(60) Provisional application No. 62/539,923, filed on Aug. 1, 2017.

(30) Foreign Application Priority Data

Aug. 21, 2017   (EP) ..................................... 17187094

(51) Int. Cl.
*C02F 3/28*    (2006.01)
*C02F 11/04*   (2006.01)
(Continued)

(52) U.S. Cl.
CPC .............. *C12M 21/04* (2013.01); *C02F 1/722* (2013.01); *C02F 3/28* (2013.01); *C02F 3/30* (2013.01);
(Continued)

(58) Field of Classification Search
CPC .......... C12M 21/04; C12M 29/18; C02F 3/28; C02F 11/04; C02F 11/06; C02F 11/12;
(Continued)

(56) References Cited

U.S. PATENT DOCUMENTS 8,637,299 B2 *   1/2014  Heichberger ............. C12P 7/64
                                                           435/262
2012/0241387 A1  9/2012  Hussain et al.
(Continued)

FOREIGN PATENT DOCUMENTS

EP    0 220 647 A1    5/1987
JP    2002-361291 A  12/2002
(Continued)

OTHER PUBLICATIONS

Database WPI Week 200345, Thompson Scientific, London, GB; AN 2003-472749, XP002778242, Dec. 17, 2002.

*Primary Examiner* — Fred Prince
(74) *Attorney, Agent, or Firm* — BakerHostetler (57) ABSTRACT

An apparatus for refractory organics conversion into biogas includes an anaerobic digester configured to be fed with organic material comprising refractory organics and to generate biogas and a digestate comprising at least a part of the refractory organics, wherein the apparatus comprises a device for a controlled partial oxidation of the refractory organics comprising an inlet configured to be fed with refractory organics and means configured to control the residence time of the refractory organics within the device for a controlled partial oxidation, so as to partially degrade (Continued)

refractory organics. A method for refractory organics conversion into biogas carried out using such an apparatus is also provided.

16 Claims, 9 Drawing Sheets

(51) Int. Cl.
- *C02F 11/06* (2006.01)
- *C02F 11/12* (2019.01)
- *C02F 1/72* (2006.01)
- *C02F 3/30* (2006.01)
- *C02F 3/34* (2006.01)
- *C12M 1/107* (2006.01)
- *C12M 1/00* (2006.01)
- *C02F 103/06* (2006.01)
- *C02F 103/28* (2006.01)

(52) U.S. Cl.
CPC ............ *C02F 11/04* (2013.01); *C02F 11/06* (2013.01); *C02F 11/12* (2013.01); *C12M 29/18* (2013.01); *C02F 3/307* (2013.01); *C02F 3/342* (2013.01); *C02F 2103/06* (2013.01); *C02F 2103/28* (2013.01); *C02F 2201/3223* (2013.01); *C02F 2303/18* (2013.01); *C02F 2305/026* (2013.01); *Y02E 50/30* (2013.01); *Y02W 10/37* (2015.05)

(58) Field of Classification Search
CPC   C02F 2103/06; C02F 2305/026; C02F 3/307; C02F 3/342; C02F 2103/28; C02F 2201/3223; C02F 2303/18; C02F 1/722; C02F 3/30; Y02E 50/30; Y02W 10/37
USPC ........ 210/603, 605, 621, 622, 623, 630, 259
See application file for complete search history.

(56) References Cited

U.S. PATENT DOCUMENTS

| | | | |
|---|---|---|---|
| 2013/0032547 A1* | 2/2013 | Pillai | C02F 1/30 210/748.16 |
| 2013/0040349 A1* | 2/2013 | Heichberger | C11C 3/003 435/134 |
| 2015/0132810 A1* | 5/2015 | Hickey | C12P 7/16 435/132 |
| 2019/0112246 A1* | 4/2019 | MacGregor | C07C 31/04 |

FOREIGN PATENT DOCUMENTS

| | | |
|---|---|---|
| WO | 20050012191 A2 | 2/2005 |
| WO | 2011/053362 A1 | 5/2011 |

* cited by examiner

APPARATUS AND METHOD FOR REFRACTORY ORGANICS CONVERSION INTO BIOGAS

CROSS-REFERENCE TO RELATED APPLICATIONS

This application is a National Stage of International patent application PCT/EP2018/070639, filed on Jul. 30, 2018, which claims priority to U.S. Provisional Patent Application No. 62/539,923 filed Aug. 1, 2017, and to foreign European patent application No. EP 17187094.2, filed on Aug. 21, 2017, the disclosures of which are incorporated by reference in their entireties.

TECHNICAL FIELD OF THE INVENTION

The invention relates to the field of waste and wastewater treatment and concerns an apparatus for refractory organics conversion into biogas. The invention also concerns a method for refractory organics conversion into biogas, and aims at reducing the refractory organics while increasing biogas production.

BACKGROUND

Anaerobic digestion produces biogas as a result of the biological fermentation of organic material supplied with the feedstock. Digesters treating complex organic substrates achieve generally between 30 and 60% of volatile solids reduction. The digestate may be dewatered to produce a cake with typically 20 to 30% solids.

Refractory organics, such as humic compounds, are organic substrates difficult to hydrolyze in absence of oxygen/under anoxic conditions. Hence, their depolymerisation becomes necessary in an anaerobic digestion setting, upstream the digestion process. Anaerobic digestion may be boosted by a thermal hydrolysis pretreatment upstream the digester.

Nevertheless landfill leachates and thermal hydrolysis pre-treated anaerobic digestion centrate and/or sludge can significantly add to the nitrogen, refractory chemical oxygen demand (also called COD) and colloidal material load of a wastewater treatment plant. In this patent application, the term "refractory organics" includes organic nitrogen, refractory COD and/or colloidal material.

On the one hand, this organic load is inhibitory to both the anaerobic ammonium oxidation and ammonia-oxidizing bacteria populations. Consequently, these compounds result in decreasing the biological activity when a side stream treatment is installed. On the other hand, these compounds lead to an increase of the effluent nitrogen and carbon, thus making it difficult to meet the discharge limits and/or requirements. Additionally, they also quench UV light on wastewater treatment plant outlets, resulting in the reduction of the disinfection efficiency of such systems.

Most biomass pre-treatment technologies for biogas production have their yield limited by a threshold. The latter is due to the partial bio-availability and bio-degradability of the carbon to the methanogenic population. Consequently, the effluent of the above-mentioned processes can be heavily loaded in refractory chemical oxygen demand (COD) and colloidal material load.

An existing solution consists in returning the effluent to headworks for a conventional carbon treatment using aeration tanks. This solution leads to an increase of oxygen/air consumption in the aeration tanks to eliminate the additional carbon and remain within rejection criteria. Therefore there is an increase of the electrical needs to aerate the aeration tanks and an increase of the production of biological sludge to be treated.

Another existing solution consists in implementing a Fenton oxidation process on the effluent. Such a solution is not satisfying since this oxidation leads to the carbon destruction that is to say that the carbon is not valued as it could be.

SUMMARY OF THE INVENTION

The invention aims to provide a solution to increase the biogas production with low aeration requirements and headworks return and using the carbon to produce energy and increase the overall biogas yield instead of producing $CO_2$. The invention allows achieving a low reagent consumption to maximize the biogas production within a small reactor design.

To this end, a subject of the invention is an apparatus for refractory organics conversion into biogas comprising an anaerobic digester configured to be fed with organic material comprising refractory organics and to generate biogas and a digestate comprising at least a part of the refractory organics, the apparatus comprising a device for a controlled partial oxidation of the refractory organics comprising an inlet configured to be fed with refractory organics and means configured to control the residence time of the refractory organics within the device for a controlled partial oxidation, so as to partially degrade refractory organics. The partial degradation of the refractory organics maximizes the generation of single rings and acetate and minimizes $CO_2$ production.

Advantageously, the anaerobic digester comprises a recirculation loop configured to recirculate the at least a part of the refractory organics degraded by the device for a controlled partial oxidation back into the anaerobic digester, and the device for a controlled partial oxidation is located on the recirculation loop. A part of the refractory organics is partially degraded: macromolecules are split into smaller molecules which are then brought back into the anaerobic digester. All the carbon contained in the refractory organics can be valued.

In another embodiment according to the invention, the apparatus comprises a recirculation loop configured to recirculate the refractory organics degraded by the device for a controlled partial oxidation back into the organic material, and the device for a controlled partial oxidation is located on the recirculation loop.

Advantageously, the apparatus according to the invention comprises a dewatering unit configured to dewater the digestate from the anaerobic digester, so as to lead to a solid cake and a liquid centrate.

Advantageously, the apparatus according to the invention is arranged in such a way that at least a part of the liquid centrate is intended to be fed to the device for a controlled partial oxidation connected to an inlet of the anaerobic digester. This enables to partially degrade the refractory organics contained in the liquid centrate, especially the COD and the colloidal material.

Advantageously, the apparatus according to the invention comprises a dewatering unit configured to dewater the organic material, so as to lead to a solid cake and a liquid centrate, the liquid centrate being intended to be fed to the anaerobic digester. This results in the fact that the refractory organics contained in the liquid centrate are not released in the environment.

Advantageously, the apparatus according to the invention further comprises a unit for $H_2O_2$ removal intended to be located downstream the device for a controlled partial oxidation. It enables to degrade the hydrogen peroxide ($H_2O_2$) used for the controlled partial oxidation to oxygen if the residual $H_2O_2$ content is too high for the downstream methanogenic process.

Advantageously, the device for a controlled partial oxidation is a device for ozonation, a device for injecting $H_2O_2$ and/or $Cl_2$ and/or $ClO_2$, a Fenton, an electro-Fenton or a photo-Fenton. Such a device enables to perform a controlled partial oxidation, thus controlling the carbon depolymerisation. It leads to a lower reagent consumption ($H_2O_2$ and $Fe^{3+}$), compared to a full mineralization process since the invention aims to produce biodegradable organics (VFA/Acetate) and not $CO_2$. It also leads to an increase of the biogas production and a short contact time in the device. Since the Hydraulic Retention Time (HRT) of the effluent in the Fenton reactor is of about one minute to achieve the required form of biodegradable carbon, this minimizes the size of the Fenton reactor in comparison to a reactor used for a full mineralization process.

Advantageously, the degradation of the refractory organics leading to the formation of soluble organic molecules, the apparatus according to the invention further comprises a control loop to control input parameters of the device for a controlled partial oxidation as a function of the quantity of soluble organic molecules downstream of the device for a controlled partial oxidation. This embodiment enables to control the oxidation of the refractory organics by modifying input parameters when necessary.

Advantageously, said soluble organic molecules are chosen among the group comprising Volatile Fatty Acids, sugars, amino acids, fatty acids, monomers, oligomers.

The invention also relates to a method for refractory COD conversion into biogas within an apparatus for refractory organics conversion into biogas comprising an anaerobic digester configured to be fed with organic material comprising refractory COD and to generate biogas and a digestate comprising at least a part of the refractory organics, comprising a step of providing refractory organics to a device for a controlled partial oxidation of the refractory organics and a step of controlling the residence time of the refractory organics within the device for a controlled partial oxidation, so as to partially degrade the refractory organics.

Advantageously, the method according to the invention further comprises a step of recirculating at least a part of the refractory organics degraded by the device for a controlled partial oxidation in a recirculation loop back into the anaerobic digester and/or the organic material.

Advantageously, the method according to the invention comprises a step of feeding the digestate from the anaerobic digester into a dewatering unit configured to dewater the digestate from the anaerobic digester, leading to a solid cake and a liquid centrate.

Advantageously, the method according to the invention comprises a step of feeding at least a part of the liquid centrate to the device for a controlled partial oxidation connected to an inlet of the anaerobic digester.

Advantageously, the method according to the invention comprises a step of feeding the organic material into a dewatering unit, so as to lead to a solid cake and a liquid centrate, the liquid centrate being fed to the anaerobic digester.

Advantageously, the method according to the invention comprises a step of feeding an outlet of the device for a controlled partial oxidation to a unit for $H_2O_2$ removal.

Advantageously, the method according to the invention comprises a step of controlling input parameters of the device for a controlled partial oxidation as a function of a quantity of soluble organic molecules formed by the degradation of the refractory organics downstream of the device for a controlled partial oxidation.

BRIEF DESCRIPTION OF THE DRAWINGS

The accompanying drawings illustrate various non-limiting, exemplary, innovative aspects in accordance with the present description.

For the sake of clarity, the same elements have the same references in the various figures.

DETAILED DESCRIPTION

On the figures:

References 10, 20, 30, 40, 50, 60, 70, 80, 90, 100, 110, 120, 130, 140, 150 designate apparatuses according to different embodiments of the invention.

Reference 11 designates an anaerobic digester.

Reference 12 designates organic material.

Reference 13 designates biogas.

References 9 and 14 designate a digestate.

Reference 15 designates a device for controlled partial oxidation.

Reference 16 designates a recirculation loop.

Reference 17 designates a dewatering unit.

References 18 and 28 designate a solid cake.

Reference 19 and 29 designate a liquid centrate.

Reference 21 designates a set of control input parameters.

Reference 22 designates a control loop.

Reference 23 designates a control variable, for instance a quantity of soluble organic molecules.

Reference 24 designates a set point for control variable 23.

Reference 25 designates a unit for $H_2O_2$ removal.

Reference E designates an error signal.

Figure 16:
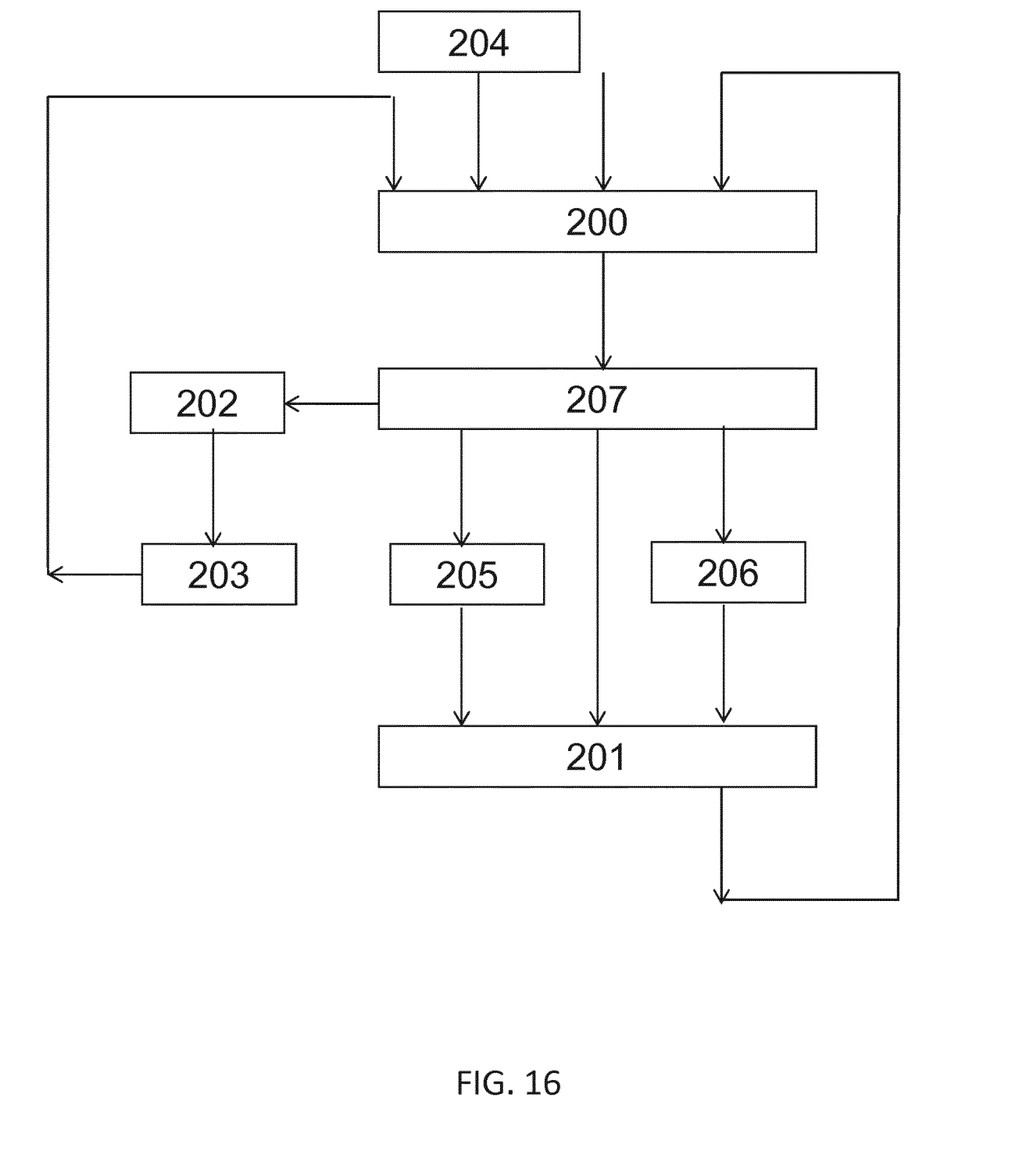
FIG. 16 schematically represents a block diagram with the step(s) of a method for refractory organics conversion into biogas according to the invention.

Reference 200 designates a step of providing at least a part of a refractory organics to a device for a controlled partial oxidation.

Reference 201 designates a step of recirculating at least a part of the refractory organics degraded by the device for a controlled partial oxidation in a recirculation loop back into an anaerobic digester.

Reference 202 designates a step of feeding a digestate from the anaerobic digester into a dewatering unit.

Step 203 designates a step of feeding a part of a liquid centrate from the dewatering unit to the device for controlled partial oxidation.

Step 204 designates a step of feeding the organic material into a dewatering unit so as to lead to a solid cake and a liquid centrate, and of feeding the liquid centrate to the anaerobic digester.

Step 205 designates a step of feeding an outlet of the device for controlled partial oxidation to a unit for $H_2O_2$ removal.

Step 206 designates a step of controlling input parameters of the device for controlled partial oxidation as a function of a quantity of soluble organic molecules formed by the degradation of the refractory organics downstream of the device for a controlled partial oxidation.

Step 207 designates a step of controlling the residence time of the refractory organics within the device for a controlled partial oxidation.

Figure 1:
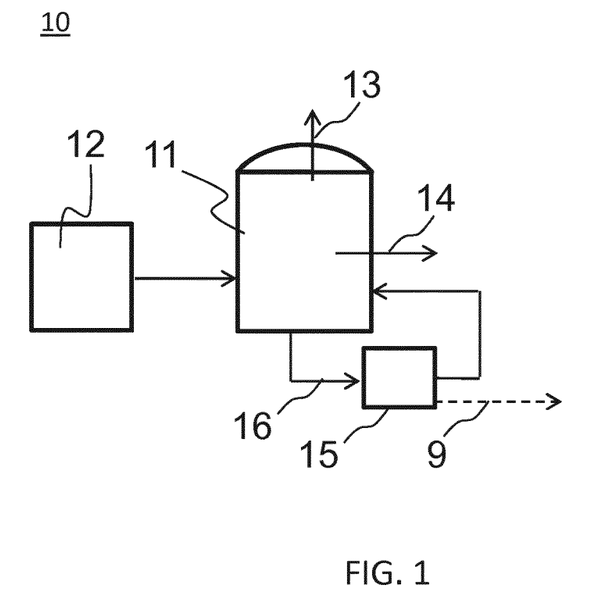
FIG. 1 schematically represents a first embodiment of the apparatus for refractory organics conversion into biogas according to the invention.

FIG. 1 schematically represents a first embodiment of the apparatus for refractory organics conversion into biogas according to the invention. The apparatus 10 for refractory organics conversion into biogas 13 comprises an anaerobic digester 11 configured to be fed with organic material 12 comprising refractory organics and to generate biogas 13 and a digestate 14 comprising at least a part of the refractory organics. According to the invention, the apparatus 10 comprises a device for a controlled partial oxidation 15 of the refractory organics comprising an inlet configured to be fed with refractory organics and means configured to control the residence time of the refractory organics within the device for a controlled partial oxidation, so as to partially degrade refractory organics. The means configured to control the residence time of the refractory organics within the device for a controlled partial oxidation ensure that the refractory organics stay within the device 15 for a duration enabling to split the refractory chains into smaller chains without a complete oxidation to avoid $CO_2$ production. In other words, the means configured to control the residence time of the refractory organics within the device for a controlled partial oxidation enable a residence time within the device 15 long enough to degrade refractory organics and not too long to obtain a partial oxidation of the refractory organics. The means configured to control the residence time of the refractory organics within the device for a controlled partial oxidation may be a timer, or a time controller coupled to an analyser configured to analyse the output of the device 15 and adapt the residence time depending on the output analysis from the analyser.

The device for a controlled partial oxidation 15 may be a device for ozonation, a device for injecting $H_2O_2$ and/or $Cl_2$ and/or $ClO_2$, a Fenton, an electro-Fenton or a photo-Fenton. The aim of such a device is to transform the refractory chains of the refractory organics into smaller chains. This partial mineralization enables to control the carbon depolymerisation. Therefore the $CO_2$ production is minimized.

The photo-Fenton process can provide a robust and commercially proven alternative approach for refractory COD and organic nitrogen depolymerisation into single ring products, without the need of harsh acidic or alkaline treatment. The reaction was shown to successfully mineralize humic acids (HA) into $CO_2$ under mild conditions (initial pH 4.0, $H_2O_2$ 160 mM, Fe2+ 40 mM, reaction time 120 min, reaction temperature 30° C. The reaction can be summarized as follow:

$$Fe^{2+}+H_2O_2 \rightarrow Fe^{3+}+HO.+OH-$$

$$Fe^{3+}+H_2O_2 \rightarrow Fe^{2+}+HOO.+H+$$

The free radicals generated by this process are powerful, non-selective oxidant capable of oxidising organic compound such as HA into carbon dioxide and water.

In contrast, the photo-Fenton reaction uses light to regenerate the iron (II), which was shown to increase the degradation rate of organic substances as more OH radicals are being generated, according to:

$$Fe^{3+}+H_2O_2+h\nu \rightarrow Fe^{2+}+HO.+H^+$$

Significantly smaller quantities of hydrogen peroxide and iron are needed, which provides the advantage of lower OPEX, minimizes further separation of the iron ions downstream and allows to significantly slow down the reaction by turning off the light source when needed. As an example, the degradation of humic acids (HA) can be carried out during the photo Fenton reaction in aqueous solutions at pH 5.0, with $Fe^{3+}$ and $H_2O_2$, under a 500 W irradiation ($\lambda > 370$ nm). A decrease in the concentration of total organic carbon (TOC) with increasing irradiation time can be shown, indicating that the molecular size of HA decreased as a result of the irradiation. Furthermore, it was shown that large molecular weight component in HA appears to be more easily degraded by the photo-Fenton process compared to the smaller components. The digester may operate at a different pH. The irradiance may be a control parameter of the reaction rate and also depends on the size/design of the apparatus.

The classical Fenton process is commonly used to mineralize recalcitrant hydrocarbons and chemicals into $CO_2$, which is not desired. On top of the additional means needed to post-treat $CO_2$, the total amount of carbon is not valued as it could be since $CO_2$ is rejected.

The invention is based on the use of the Fenton reaction to degrade the refractory organics present in landfill leachates and thermal hydrolysis pre-treated anaerobic digestion centrate and/or sludge. Thermal treatments (thermal hydrolysis THP or hydrothermal carbonization HTC) generate refractory organics. In order to obtain a controlled partial oxidation, the Fenton reaction is stopped at acetate or single rings organics that are easily degradable anaerobically. Retention time of the media in the Fenton reactor can be calibrated to minimize $CO_2$ production and maximize the generation of single ring and acetate.

In order to offset this energy expenditure, solar energy may be used to generate electricity through photovoltaic panels. Another option is to use a solar photo-Fenton reaction.

Addition of $H_2O_2$ and Fe(III) is the only requirement for the reaction to take place.

The device for a controlled partial oxidation 15 being a classical Fenton, the reaction is controlled by the residence time in the reactor and the quantity of $H_2O_2$ and $Fe^{2+}$. The device for a controlled partial oxidation 15 being an electro-Fenton, the reaction is controlled by the residence time in the reactor and the quantity of $H_2O_2$ since the cathode of the electro-Fenton generates iron. The device for a controlled partial oxidation 15 being a photo-Fenton, the reaction is controlled by the residence time in the reactor and the quantity of $H_2O_2$ and irradiance. In this preferred embodiment, the control of the device 15 may be performed by modifying irradiance or stopping it to modify or stop the reaction in the device 15. This enables an increased control of the reaction.

Furthermore, since a controlled partial oxidation takes place in the device 15, a shorter contact time (within minutes) is enough for the partial oxidation. This leads to smaller reactor design for a predetermined quantity to treat.

Partially converted soluble organic molecules (e.g. Volatile Fatty Acids VFA) may be evacuated from device 15 (ref. 9). At least part of the refractory organics degraded by the device for a controlled partial oxidation 15 is recirculated back into the anaerobic digester 11.

According to a preferred embodiment, the anaerobic digester 11 comprises a recirculation loop 16 configured to recirculate the at least a part of the refractory organics degraded by the device for a controlled partial oxidation 15 back into the anaerobic digester 11, and the device for a controlled partial oxidation 15 is located on the recirculation loop 16. All the flux of carbon is treated. The refractory organics flows into the recirculation loop. This increases the biogas production.

Figure 2:
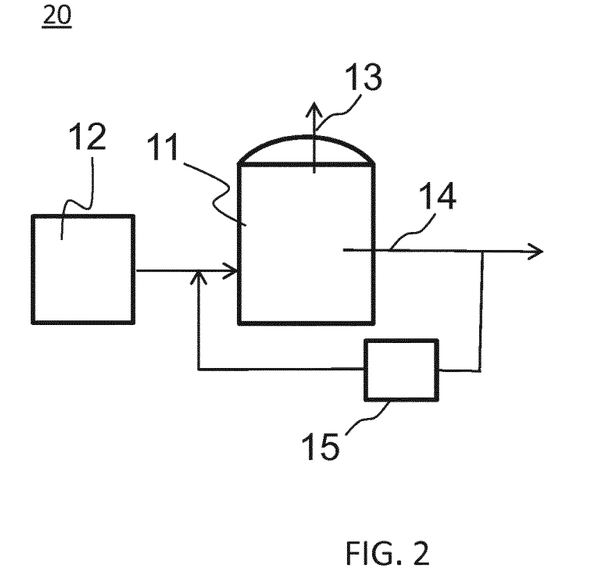
FIG. 2 schematically represents another embodiment of the apparatus for refractory organics conversion into biogas according to the invention.

FIG. 2 schematically represents another embodiment of the apparatus 20 for refractory organics conversion into biogas according to the invention. The elements of the apparatus 20 are identical to those of the apparatus 10. In FIG. 2, the digestate 14 is fed to the device for a controlled partial oxidation 15, and at least part of the refractory organics degraded by the device for a controlled partial oxidation 15 is recirculated back into an inlet of the anaerobic digester 11. The controlled partial oxidation leads to an acetate/VFA/single rings rich solution acetate. Therefore, a clear acetate/VFA/single rings rich media in recirculated back into the anaerobic digester 11.

Figure 3:
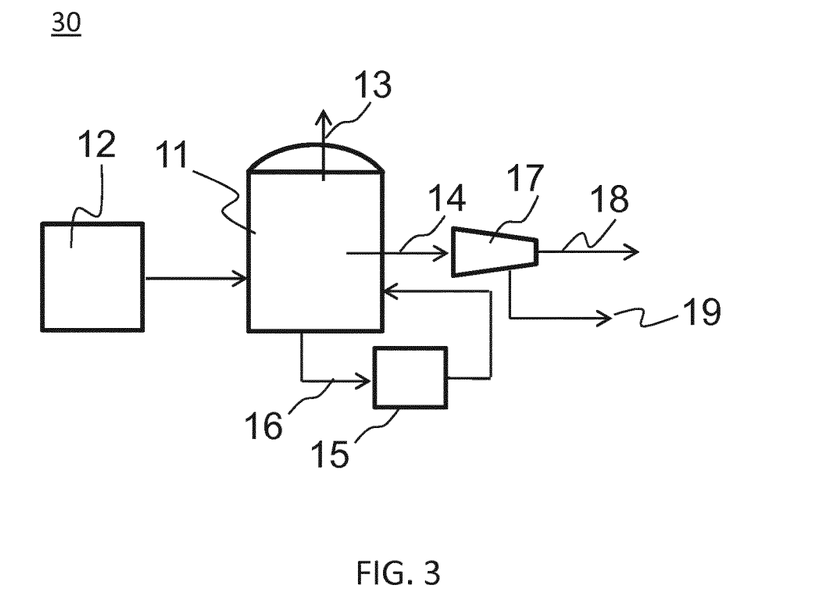
FIG. 3 schematically represents another embodiment of the apparatus for refractory organics conversion into biogas according to the invention.

FIG. 3 schematically represents another embodiment of the apparatus 30 for refractory organics conversion into biogas according to the invention. The elements of the apparatus 30 are identical to those of the apparatus 10. The apparatus 30 comprises a dewatering unit 17 configured to dewater the digestate 14 from the anaerobic digester 11, so as to lead to a solid cake 18 and a liquid centrate 19. The separation of the solid cake 18 on the one hand and the liquid centrate 19 on the other hand enable to treat these compounds separately.

In the apparatus 30, the dewatering unit 17 is located downstream the anaerobic digester 11 to treat the digestate 14 of the anaerobic digester 11.

Figure 4:
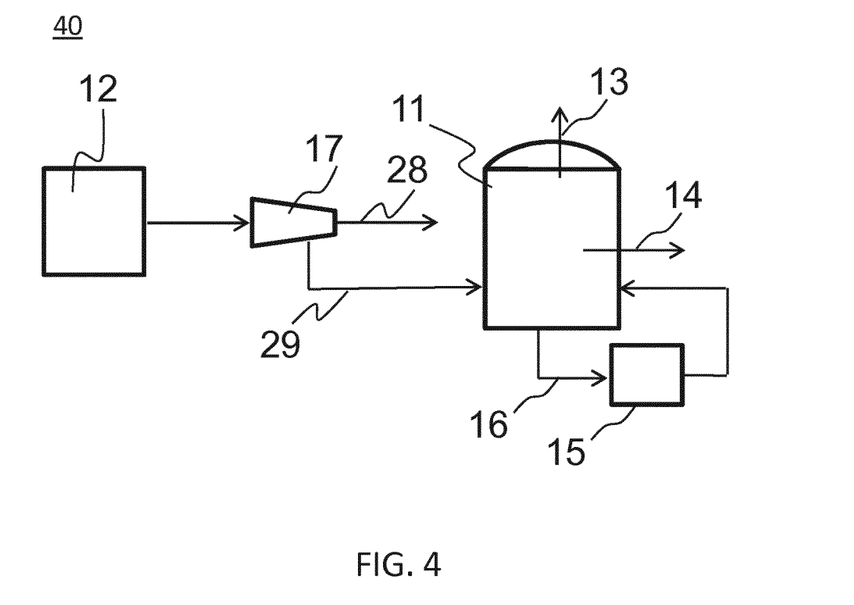
FIG. 4 schematically represents another embodiment of the apparatus for refractory organics conversion into biogas according to the invention.

FIG. 4 schematically represents another embodiment of the apparatus 40 for refractory organics conversion into biogas according to the invention. The elements of the apparatus 40 are identical to those of the apparatus 10. The apparatus 40 comprises a dewatering unit 17 configured to dewater the organic material 12, so as to lead to a solid cake 28 and a liquid centrate 29, the liquid centrate 29 being intended to be fed to the anaerobic digester 11. The liquid centrate 29 is rich in iron ions $Fe^{2+}$, which further participate to the Fenton reaction.

Generally, the invention applies preferably to an organic material 12 which is preferably liquid with few colloidal material so as to be easily assimilated by the bacteria in the anaerobic digester 11.

Figure 5:
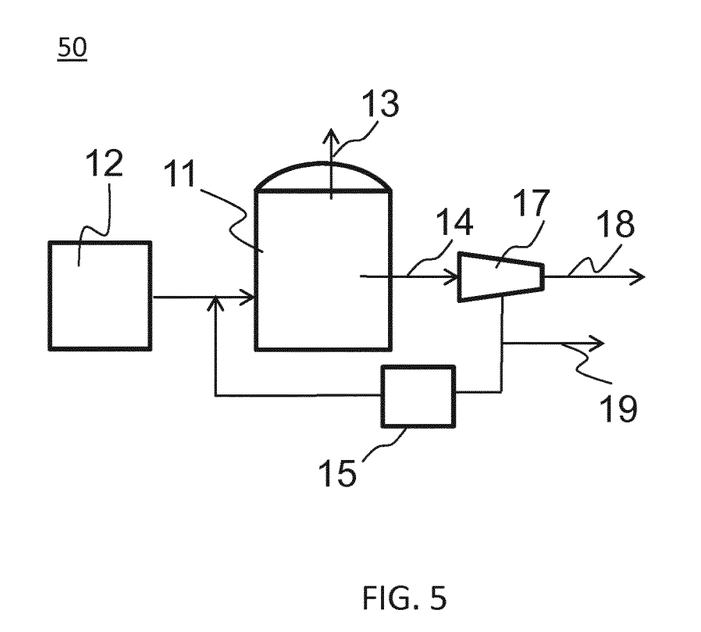
FIG. 5 schematically represents another embodiment of the apparatus for refractory organics conversion into biogas according to the invention.

FIG. 5 schematically represents another embodiment of the apparatus 50 for refractory organics conversion into biogas according to the invention. The apparatus 50 of FIG. 5 is similar to the apparatus 20 of FIG. 2, except in that it further comprises a dewatering unit 17 fed with digestate 14 and producing a solid cake 18 and a liquid centrate 19, featuring the same advantages as explained before.

Figure 6:
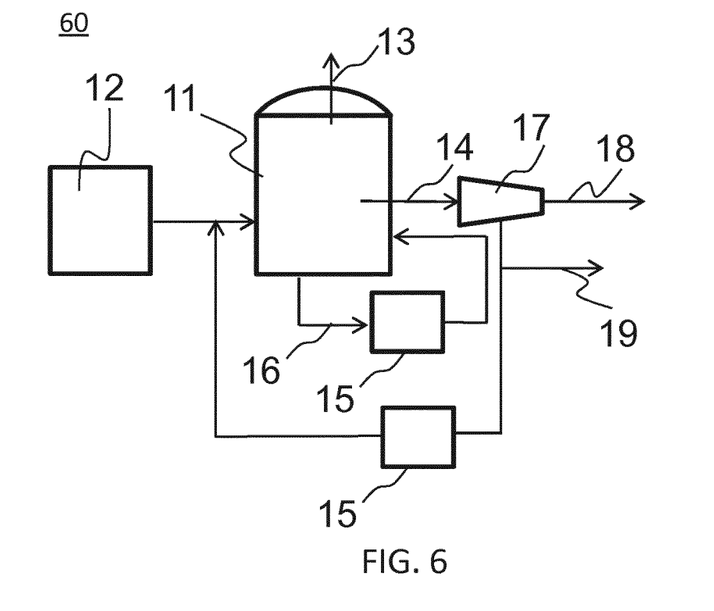
FIG. 6 schematically represents another embodiment of the apparatus for refractory organics conversion into biogas according to the invention.

FIG. 6 schematically represents another embodiment of the apparatus 60 for refractory organics conversion into biogas according to the invention. The apparatus 60 of FIG. 6 is similar to the apparatus 50 of FIG. 5, except in that it further comprises a second recirculation loop recirculating at least part of the liquid centrate 19 into the anaerobic digester 11. This second recirculation loop comprises a second device for a controlled partial oxidation 15. This configuration enables to both recirculate a part of the refractory organics back into the anaerobic digester 11 and recirculate the clear acetate rich media back into an inlet of the anaerobic digester 11. This increases the biogas 13 production.

FIGS. 7 to 12 schematically represent another embodiment of the apparatus 70, 80, 90, 100, 110, 120 for refractory organics conversion into biogas presented in FIGS. 1 to 6 respectively according to the invention.

Figure 7:
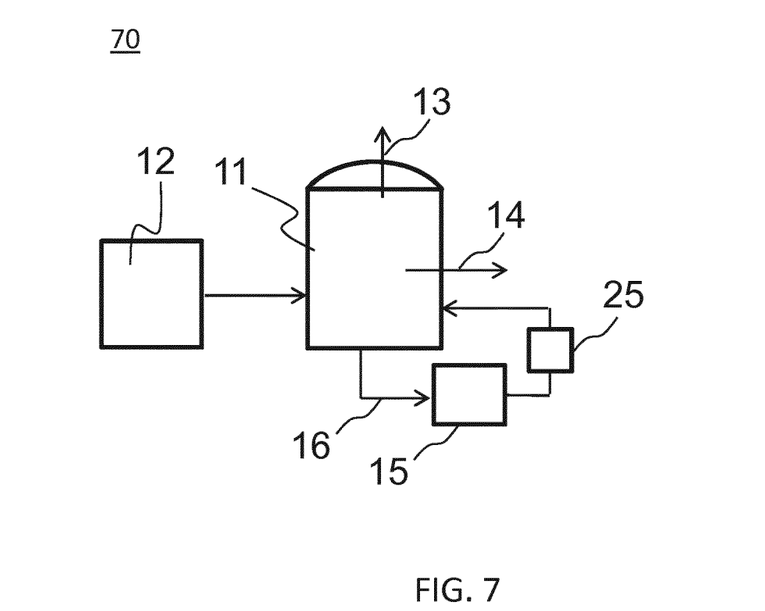
FIGS. 7 to 12 schematically represent another embodiment of the apparatus for refractory organics conversion into biogas presented in FIGS. 1 to 6 respectively according to the invention.

The apparatus 70 of FIG. 7 is similar to the apparatus 10 of FIG. 1, except in that it further comprises a unit for $H_2O_2$ removal 25 situated in the recirculation loop, downstream the device for a controlled partial oxidation 15.

Figure 8:
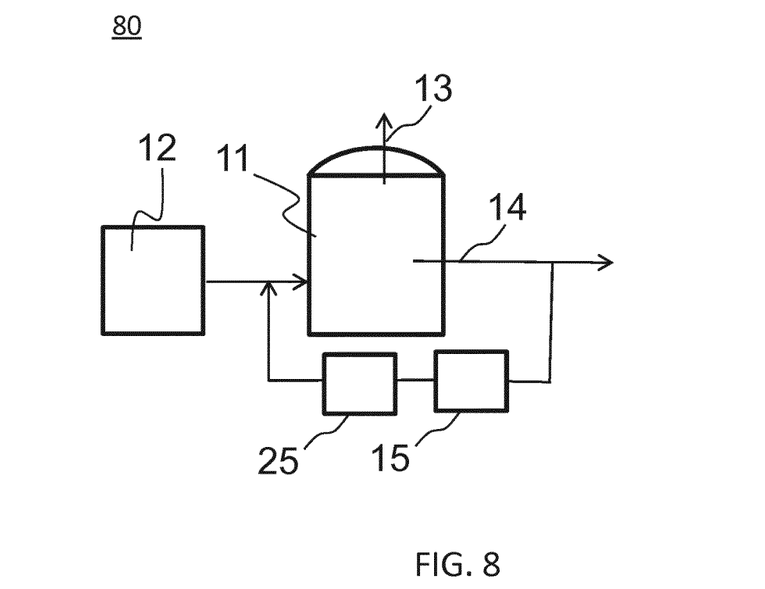

The apparatus 80 of FIG. 8 is similar to the apparatus 20 of FIG. 2, except in that it further comprises a unit for $H_2O_2$ removal 25 situated in the recirculation loop, downstream the device for a controlled partial oxidation 15.

Figure 9:
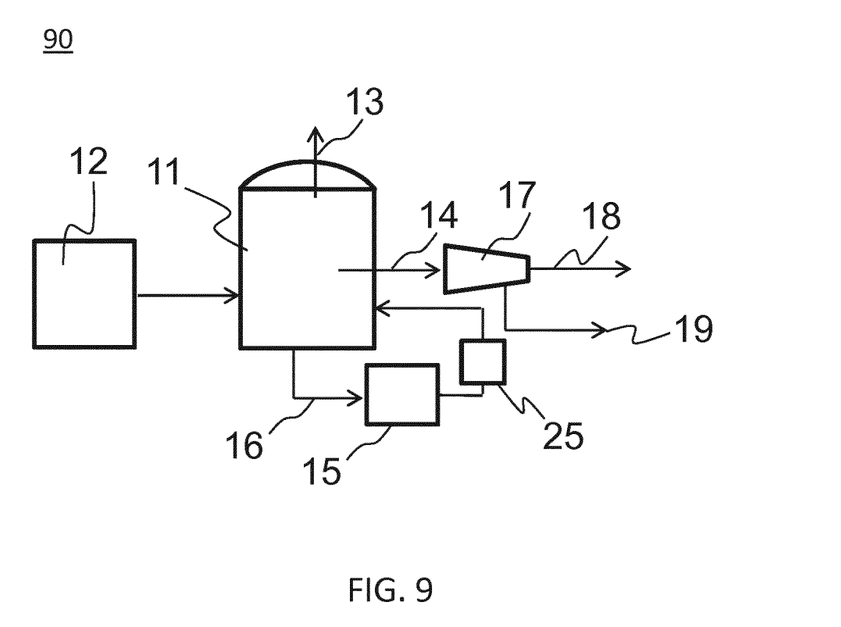

The apparatus 90 of FIG. 9 is similar to the apparatus 30 of FIG. 3, except in that it further comprises a unit for $H_2O_2$ removal 25 situated in the recirculation loop, downstream the device for a controlled partial oxidation 15.

Figure 10:
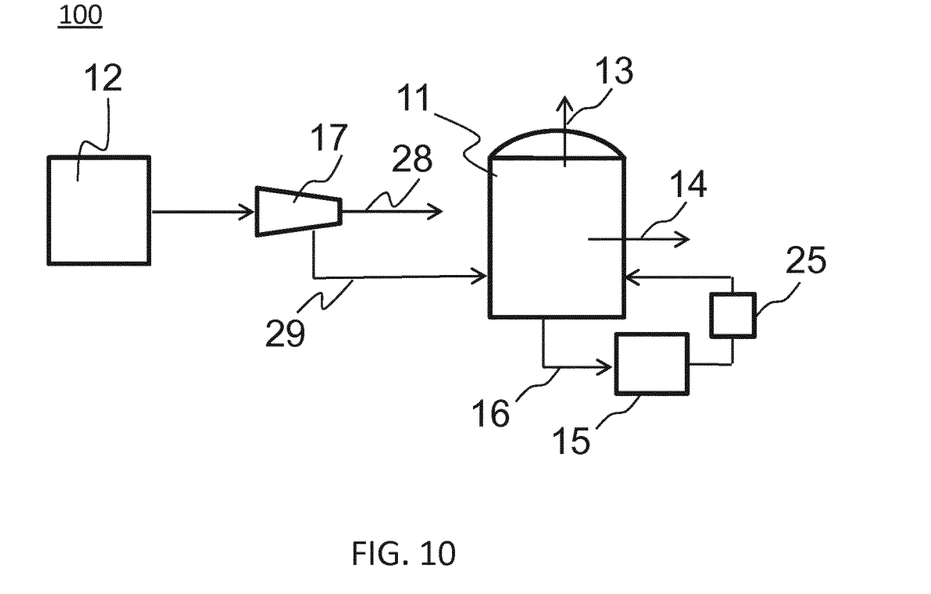

The apparatus 100 of FIG. 10 is similar to the apparatus 40 of FIG. 4, except in that it further comprises a unit for $H_2O_2$ removal 25 situated in the recirculation loop, downstream the device for a controlled partial oxidation 15.

Figure 11:
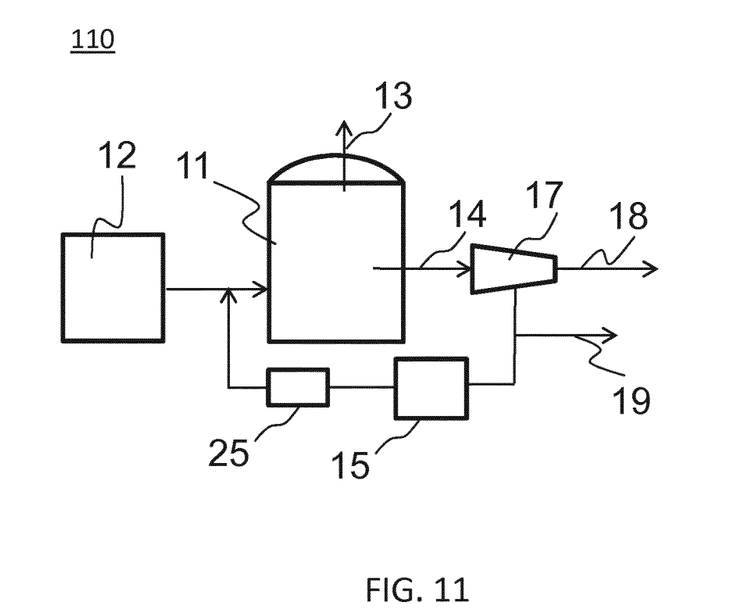

The apparatus 110 of FIG. 11 is similar to the apparatus 50 of FIG. 5, except in that it further comprises a unit for $H_2O_2$ removal 25 situated in the recirculation loop, downstream the device for a controlled partial oxidation 15.

Figure 12:
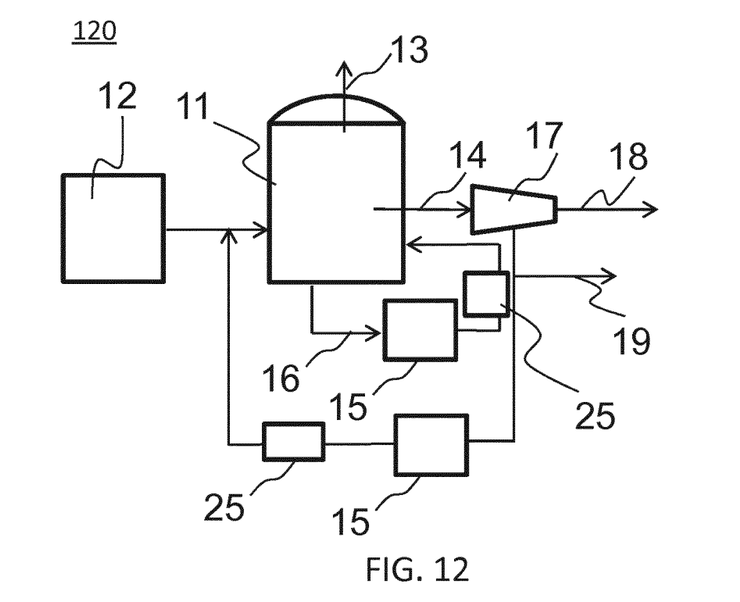

The apparatus 120 of FIG. 12 is similar to the apparatus 60 of FIG. 6, except in that it further comprises a unit for $H_2O_2$ removal 25 situated in each of the recirculation loop, downstream the respective device for a controlled partial oxidation 15.

The unit for $H_2O_2$ removal 25 enables to degrade the hydrogen peroxide ($H_2O_2$) used for the controlled partial oxidation to oxygen if the residual $H_2O_2$ content is too high for the downstream methanogenic process. The unit for $H_2O_2$ removal 25 comprises enzymes that are $H_2O_2$ degrading enzymes, such as catalase. Advantageously, the enzymes are immobilized in order to prevent a wash out. The treated flux coming from the device 15 for a controlled partial oxidation flows on these enzymes. $H_2O_2$ which is an unstable species is rapidly degraded.

Figure 13:
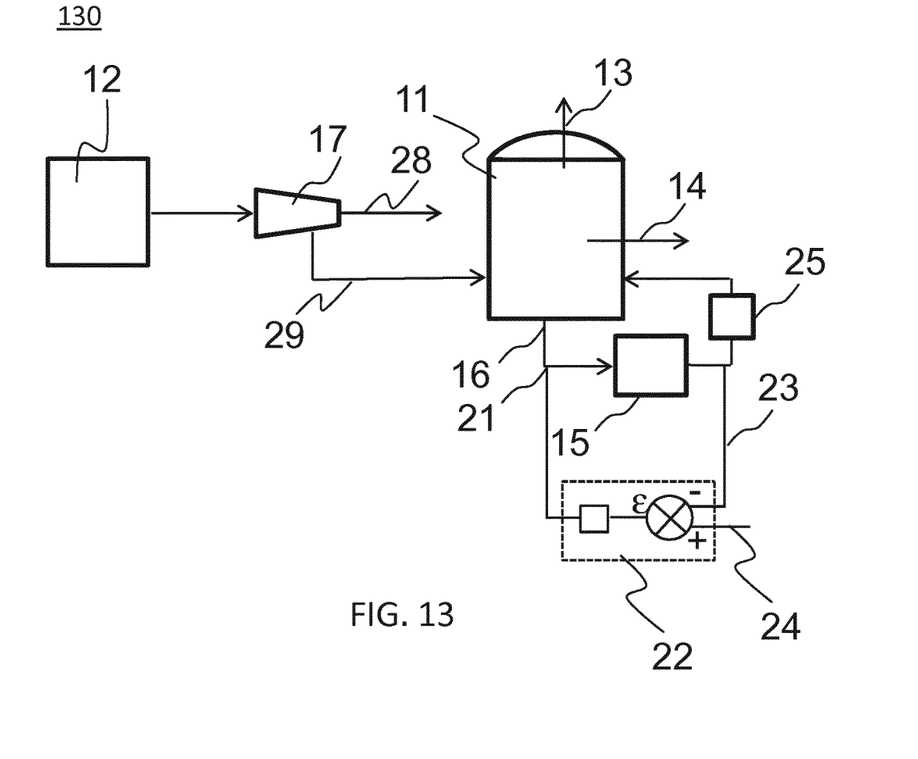
FIG. 13 schematically represents another embodiment of the apparatus for refractory organics conversion into biogas according to the invention.

FIG. 13 schematically represents another embodiment of the apparatus 130 for refractory organics conversion into biogas according to the invention. The apparatus 130 of FIG. 13 is similar to the apparatus 40 of FIG. 4, except in that it further comprises a control loop 22 to control input parameters 21 of the device for a controlled partial oxidation 15 as a function of a control variable 23, e.g. representing the quantity of soluble organic molecules downstream of the device for a controlled partial oxidation 15. More precisely, the control input parameters 21 are determined as a function of instant and/or previous values of an error signal E representing a difference between the value of control variable 23 and a set point 24. A direct measurement via infrared may be performed to determine the input parameters 21 and the control variable 23. It can be noted that the control loop 22 illustrated in FIG. 13 is only a representation of a possible control. The control may be performed on the recirculation loop and/or at the outlet of the device for a controlled partial oxidation 15.

The apparatus 130 is similar to the apparatus 40, but it is obvious that the control loop 22 can be applied to any other embodiment presented previously.

The soluble organic molecules may be chosen among the group comprising Volatile Fatty Acids, sugars, amino acids, fatty acids, monomers, oligomers.

Figure 14:
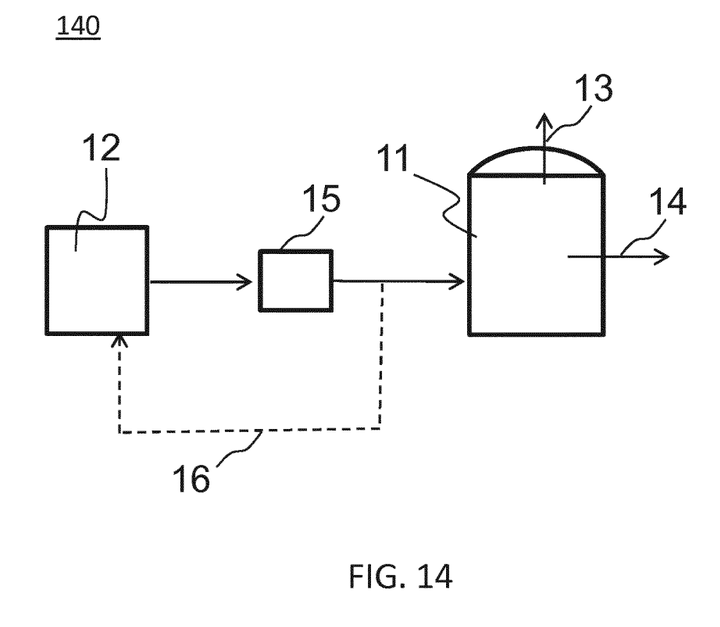
FIGS. 14 and 15 schematically represent other embodiments of the apparatus for refractory organics conversion into biogas according to the invention.
Figure 15:
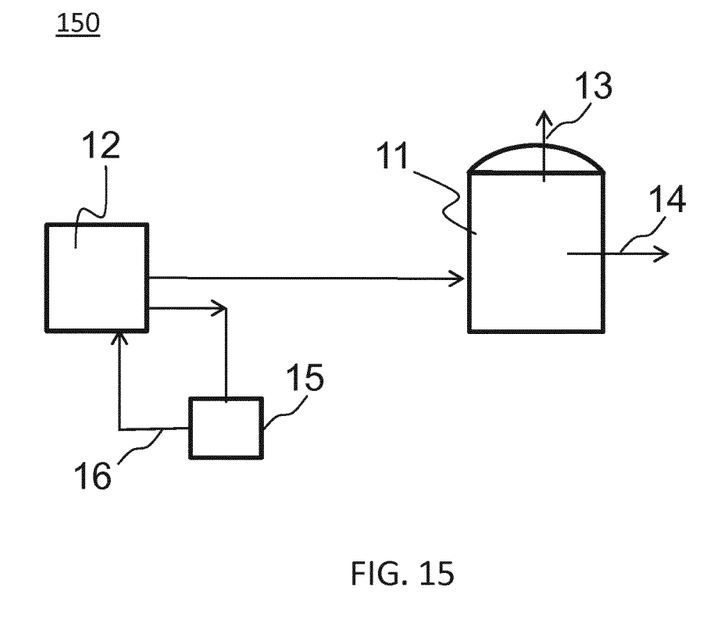

FIGS. 14 and 15 schematically represent other embodiments of the apparatuses 140, 150 for refractory organics conversion into biogas according to the invention. The apparatuses 140 and 150 comprise an anaerobic digester 11 configured to be fed with organic material 12 comprising refractory organics and to generate biogas 13 and a digestate 14 comprising at least a part of the refractory organics. The apparatuses 140 and 150 comprise a device for a controlled partial oxidation 15 of the refractory organics configured to partially degrade the refractory organics and the device for a controlled partial oxidation is located between the organic material 12 and the anaerobic digester 11, so as to partially degrade the refractory organics contained in the organic material 12. As represented in dotted lines on FIG. 14, the apparatus 140 may comprise a recirculation loop 16 configured to recirculate the refractory organics degraded by the device for a controlled partial oxidation 15 back into the organic material 12, thus enabling to increase the retention time of the refractory organic 12 within the device 15 for a controlled partial oxidation. In FIG. 150, the recirculation loop 16 recirculates the refractory organics degraded by the device for a controlled partial oxidation 15 into the organic material 12 and the digester 11 is fed with organic material 12, which then comprises both refractory organics and refractory organics already degraded by the device for a controlled partial oxidation 15.

The apparatuses 140 and 150 may comprise a unit for $H_2O_2$ removal located downstream the device for a controlled partial oxidation 15 (not represented on FIGS. 14-15). As explained before, this unit degrades $H_2O_2$ if the residual $H_2O_2$ content is too high for the downstream methanogenic process.

The embodiment presented in FIGS. 14-15, i.e the apparatuses 140-150 with the device for a controlled partial oxidation 15 located between the organic material 12 and the digester 11 (with or without the recirculation loop) is compatible with the embodiments presented in the previous figures and may be associated to the corresponding apparatuses. In other words, the apparatuses 10-130 may further comprise a device for a controlled partial oxidation 15 located between the organic material 12 and the digester 11 (with or without the recirculation loop between an outlet of the device 15 and the tank for organic material 12). Combined with the apparatus 40, 100 or 130 (comprising a dewatering unit to dewater the organic material 12, so as to lead to a solid cake 28 and a liquid centrate 29), the device for a controlled partial oxidation 15 is preferably located upstream the dewatering unit.

FIG. 16 schematically represents a block diagram with the step(s) of a method for refractory organics conversion into biogas according to the invention. The method for refractory COD conversion into biogas 13 within an apparatus for refractory organics conversion into biogas 13 comprising an anaerobic digester 11 configured to be fed with organic material 12 comprising refractory COD and to generate biogas 13 and a digestate 14 comprising at least a part of the refractory organics, comprises a step 200 of providing at least a part of refractory organics to a device for a controlled partial oxidation 15 of the refractory organics and a step 207 of controlling the residence time of the refractory organics within the device for a controlled partial oxidation 15, so as to partially degrade the refractory organics. The partial degradation of the refractory organics into acetate enables to increase the biogas production since most of the carbon is valued and to minimize the $CO_2$ production, even when using the Fenton process.

The method according to the invention may further comprise a step 201 of recirculating at least a part of the refractory organics degraded by the device for a controlled partial oxidation 15 in a recirculation loop 16 back into the anaerobic digester 11. The refractory organics split into smaller chains is recirculated into the digester 11, thus enabling all the carbon to be treated.

The method according to the invention may further comprise a step 202 of feeding the digestate 14 from the anaerobic digester 11 into a dewatering unit 17 configured to dewater the digestate 14 from the anaerobic digester 11, leading to a solid cake 18 and a liquid centrate 19.

The method according to the invention may further comprise a step 203 of feeding at least a part of the liquid centrate 19 to the device for a controlled partial oxidation 15 connected to an inlet of the anaerobic digester 11. This step results in the introduction into the digester of $Fe^{2+}$ ion rich centrate, which can be further fed to the Fenton process.

The method according to the invention may further comprise a step 204 of feeding the organic material 12 into a dewatering unit 17, so as to lead to a solid cake 28 and a liquid centrate 29, the liquid centrate 29 being fed to the anaerobic digester 11. This step results in the introduction into the digester of $Fe^{2+}$ ion rich centrate, which can be further fed to the Fenton process. Furthermore, the solid cake 28 is already separated from the liquid centrate 29, which means that mostly a liquid part is directed to the digester. This liquid part is easier to be assimilated by the bacteria.

The method according to the invention may further comprise a step 205 of feeding an outlet of the device for a controlled partial oxidation 15 to a unit for $H_2O_2$ removal 25. This step enables to degrade the hydrogen peroxide ($H_2O_2$) used for the controlled partial oxidation to oxygen if the residual $H_2O_2$ content is too high for the downstream methanogenic process.

The method according to the invention may further comprise a step 206 of controlling input parameters of the device for a controlled partial oxidation 15 as a function of a quantity of soluble organic molecules formed by the degradation of the refractory organics downstream of the device for a controlled partial oxidation 15. This step enables to control the retention time in the device 15 and parameters for dosing iron ions and $H_2O_2$.

The invention has a very broad application field, for example landfill/waste leachate, agro-industrial effluent, industrial effluent, paper mill effluent, waste anaerobic digestion effluent, lignocellulosic biorefinery effluent.

The invention has various related advantages, namely a reduced production of biological sludge in the aeration tank as the effluent that returns to headwork has a lower organic load, a reduction of the colloids content in the effluent, making direct sidestream treatment possible such as an Anammox (anaerobic ammonium oxidation) based process for ammonia abatement. Indeed, colloids would trap the $O_2$ content, which leads to a reduction of the nitrification step and therefore an incomplete abatement of nitrogen. Another advantage of the invention is a reduction of the amount of COD in the effluent, making direct sidestream treatment possible such as an Annamox based process for ammonia abatement. Indeed, COD promotes the development of bacteria, which decimate the annamox population due to their faster population growth. Another advantage of the invention is an Increased organic loading rate of a co-digestion site (WASTE setting): In some cases, a digester is limited in the organic load it can treat because of the effluent requirements. Indeed, depending on the downstream treatment capacity, co-digestion of thermal treatment upstream a digester cannot be possible. The present invention allows for higher COD content to be converted into methane which increases the acceptable organic load in the digester while maintaining the effluent below the authorized carbon and nitrogen content.

The embodiments described above are only provided as non-limiting examples. Additional embodiments fall within the scope of the invention, which is only defined by the appended claims.

The invention claimed is:

1. An apparatus for refractory organics conversion into biogas comprising:
   an anaerobic digester configured:
      to be fed with organic material comprising refractory organics, and to generate biogas and a digestate comprising at least a part of the refractory organics;
   the apparatus further comprising a device for a controlled partial oxidation of the refractory organics, the device for a controlled partial oxidation being a Fenton, the device comprising:
      an inlet configured to be fed with refractory organics, and
      means configured to control a residence time of the refractory organics within the device for a controlled partial oxidation, so as to partially degrade refractory organics.

2. The apparatus according to claim 1, wherein the anaerobic digester comprises a recirculation loop configured to recirculate the at least a part of the refractory organics degraded by the device for a controlled partial oxidation back into the anaerobic digester, and wherein the device for a controlled partial oxidation is located on the recirculation loop.

3. The apparatus according to claim 1, wherein the apparatus comprises a recirculation loop configured to recirculate the refractory organics degraded by the device for a controlled partial oxidation back into the organic material, and wherein the device for a controlled partial oxidation is located on the recirculation loop.

4. The apparatus according to claim 1, further comprising a dewatering unit configured to dewater the digestate from the anaerobic digester, so as to lead to a solid cake and a liquid centrate.

5. The apparatus according to claim 4, arranged in such a way that at least a part of the liquid centrate is fed to the device for a controlled partial oxidation connected to an inlet of the anaerobic digester.

6. The apparatus according to claim 1, further comprising a dewatering unit configured to dewater the organic material, so as to lead to a solid cake and a liquid centrate, the liquid centrate being intended to be fed to the anaerobic digester.

7. The apparatus according to claim 1, further comprising a unit for $H_2O_2$ removal intended to be located downstream of the device for a controlled partial oxidation.

8. The apparatus according to claim 1, the degradation of the refractory organics leading to a formation of soluble organic molecules, wherein the apparatus further comprises a control loop to control input parameters of the device for a controlled partial oxidation as a function of a quantity of soluble organic molecules downstream of the device for a controlled partial oxidation.

9. The apparatus according to claim 8, wherein said soluble organic molecules are chosen among the group comprising volatile fatty acids, sugars, amino acids, fatty acids, monomers, oligomers.

10. A method for refractory COD conversion into biogas within an apparatus for refractory organics conversion into biogas comprising an anaerobic digester configured to be fed with organic material comprising refractory COD and to generate biogas and a digestate comprising at least a part of the refractory organics,
    the method comprising:
       a step of providing refractory organics to a device for a controlled partial oxidation of the refractory organics, the device for a controlled partial oxidation being a Fenton;
       a step of controlling a residence time of the refractory organics within the device for a controlled partial oxidation, so as to partially degrade the refractory organics.

11. The method according to claim 10, further comprising a step of recirculating the refractory organics degraded by the device for a controlled partial oxidation in a recirculation loop back into the anaerobic digester and/or the organic material.

12. The method according to claim 11, further comprising a step of feeding the digestate from the anaerobic digester into a dewatering unit configured to dewater the digestate from the anaerobic digester, leading to a solid cake and a liquid centrate.

13. The method according to claim 12, further comprising a step of feeding at least a part of the liquid centrate to the device for a controlled partial oxidation connected to an inlet of the anaerobic digester.

14. The method according to claim 10, further comprising a step of feeding the organic material into a dewatering unit, so as to lead to a solid cake and a liquid centrate, the liquid centrate being fed to the anaerobic digester.

15. The method according to claim 10, further comprising a step of feeding an outlet of the device for a controlled partial oxidation to a unit for $H_2O_2$ removal.

16. The method according to claim 10, further comprising a step of controlling input parameters of the device for a controlled partial oxidation as a function of a quantity of soluble organic molecules formed by the degradation of the refractory organics downstream of the device for a controlled partial oxidation.

* * * * *